Armard V. Motsinger
INVENTOR.

United States Patent Office

Plant Pat. 3,575
Patented June 18, 1974

3,575
ILEX (HOLLY) PLANT

Armard V. Motsinger, Aberdeen, Md. (140 W. 4th St., Windmill Village, North Fort Myers, Fla. 33903)

Filed June 22, 1971, Ser. No. 155,492
Int. Cl. A01h 5/00
U.S. Cl. Plt.—65 1 Claim The present invention relates to a new variety of the American holly plant, or *Ilex opaca,* which was produced by me by attempting to cross a female *Ilex opaca* plant with pollen from a *Viburnum rhytidophyllum* plant, however, such a cross would be against all accepted scientific principles. Both of these plants were unnamed and unpatented evergreens.

Figure 7:
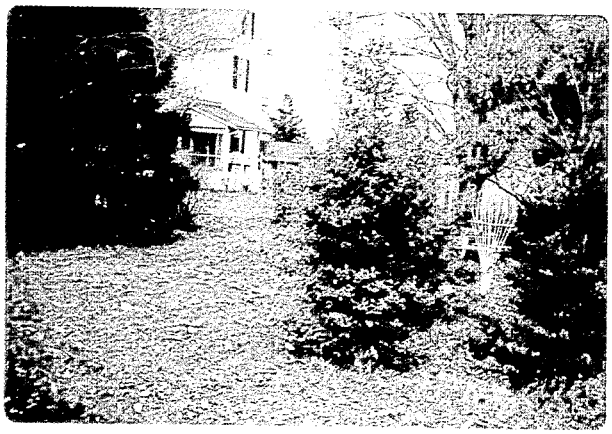
Figure 1:
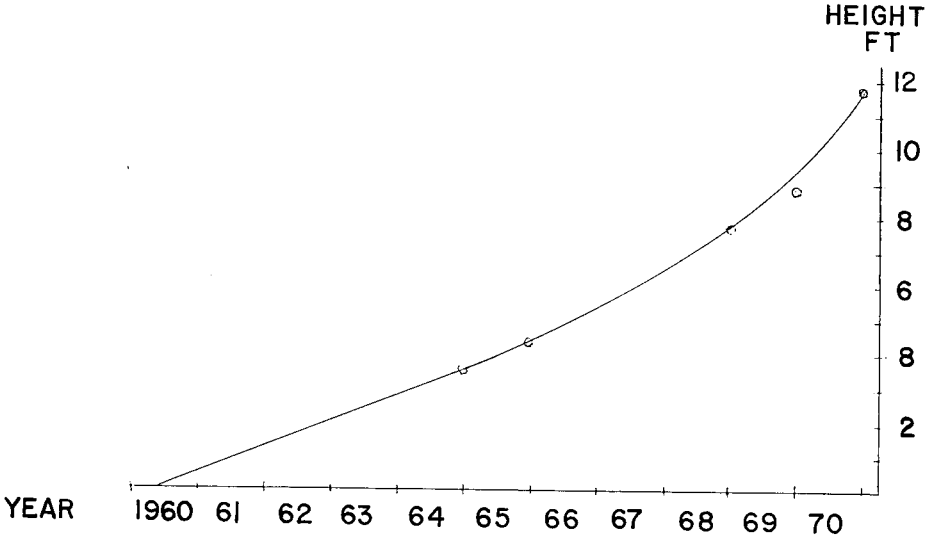
Figure 2:
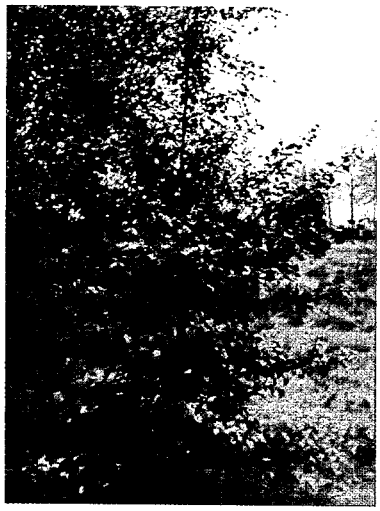
Figure 3:
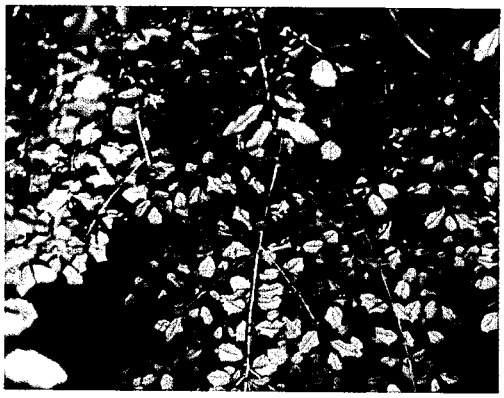
Figure 4:
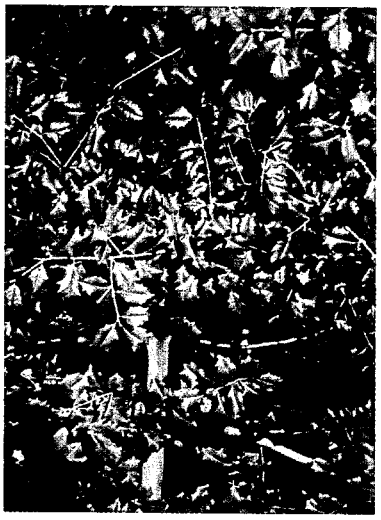
Figure 5:
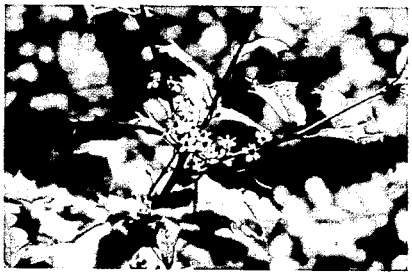
Figure 6:
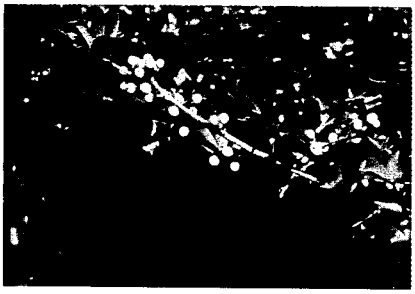

The primary objective of attempting the cross was to obtain vigorous growth and other improved characteristics in holly trees. From attempts made in 1958 and eight trees that resulted from seed in the summer of 1960, one tree has been selected for this patent, with the following characteristics:

(1) Vigorous growth in an *Ilex opaca* plant as shown by the growth chart in the drawing. The tree grew from a seedling in 1960 to a tree eleven feet nine inches tall in November 1970, with a trunk base three inches in diameter and branch spread of six feet.
(2) A female holly tree that produces an abundance of carmine colored berries (No. 6 Plate VII). (Ridgway)
(3) A holly tree of upright growth with many branches in the top half of the tree extending out at an angle of about 45 degrees from the trunk and lower branches extending almost horizontally to form an attractive pyramidal shape, medium density tree, as illustrated in the drawing.
(4) Good hardiness, ease of propagation from cuttings, and adaptability to transplanting.

In asexual reproduction of my new variety, as performed by me at Aberdeen, Md., the foregoing characteristics and distinctions have been shown to come true to form and are established and transmitted through succeeding propagations.

The accompanying colored photographs show the whole tree and close-ups of other parts of the tree, and berries, in color as nearly true as it is reasonably possible to make in a color illustration of this character. These photographs and the growth rate chart illustrate the overall characteristics of my improved variety of holly.

In general, the tree has a central leader of upright growth and has medium density foliage. It has an abundance of red berries each year and there is no noticeable change in leaf color with the production of berries, which are retained on the tree throughout the winter and some remain until blossoms are formed the following spring. The oval shaped leaves retain a glossy green color throughout the year. The tree has no single tap root, but has numerous short roots that make the tree very adaptable to transplanting. The tree shows no winter damage in Maryland. No male flowers have been observed. From its first year the subject tree, as a seedling, showed vigorous growth. This led to yearly measurements and the growth curve illustrated.

The following is a detailed description of my new variety, with color terminology in accordance with Ridgway's Color Standards and Nomenclature:

Leaves: The leaves have a dark green color (Parot green, No. 7, Plate X) on top and light geen color underneath (Dull Yellow green, No. 1, Plate XXXII). When mature the leaves have an average length of 6.7 cm.; width, 4.6 cm.; thickness 0.038 cm.; and have 4 to 7 pairs of spikes. About fifty percent of the leaves have 5 pair of spikes. The leaves are alternate on the stems, glabrous and have short petioles of about 0.5 cm. length, however, some stems have leaves that appear to be opposite; and on these stems, the petioles of the leaves originate at positions located between truly opposite and evenly alternate positions.

Branches: Glabrous; angled. The tree can be easily recognized from a distance because the neighboring adjacent main branches in the upper middle part of the tree while alternate, are nearly opposite and are at a right angle (90 degrees) to each other (each 45 degrees upward on either side of trunk) a trait resembling plants that have leaves and branches opposite.

Color stems when mature: Mouse gray, No. II, Plate II.

Color new growth stems: Dark purple, Perilla purple, Plate XXXVII, streaked and speckled with light green of the same color as the new leaves.

Flowers: 9 mm. diameter; pistillate; calyx lobed; white petals. The flowers usually have 4 petals and 4 ovaries. About 20% of the flowers have 5 petals and about 5% have 6 petals. They are produced on stems of previous seasons growth, partly in fascicles of leaves. They usually open on the 24th of May in Maryland.

Fruit: Most berries are spherical in shape 7 mm. to 9 mm. in diameter while some resemble a somewhat flattened sphere with a large diameter of 11 mm. Color: Carmine No. 6, Plate VII.

Seed: Four; 6 mm. long; color, light beige.

I claim:

1. A new and distinct plant variety of the evergreen tree type; substantially as herein described and illustrated; resulting from an attempted crossing of a Viburnum and an Ilex plant, with most characteristics including alternate branches and leaves resembling the *Ilex opaca,* but with some branches and some leaves nearly opposite, and characterized particularly as a novelty by its rapid growth; attractive red berries spread evenly among green leaves; upper middle branches extending from either side of the trunk at approximately 45 degrees giving the appearance that they extend at right angles to each other; and the entire tree having an attractive upright pyramidal shape, with profuse foliage and berries.

No references cited.

ROBERT E. BAGWILL, Primary Examiner